United States Patent [19]

Köppe et al.

[11] 4,084,002
[45] Apr. 11, 1978

[54] PHARMACEUTICAL COMPOSITIONS CONTAINING A 1-PHENOXY-2-HYDROXY-3-ALKYNYLAMINO-PROPANE AND METHOD OF USE

[75] Inventors: Herbert Köppe; Werner Kummer; Helmut Stähle; Gojko Muacevic, all of Ingelheim am Rhein, Germany

[73] Assignee: Boehringer Ingelheim GmbH, Ingelheim am Rhein, Germany

[21] Appl. No.: 742,639

[22] Filed: Nov. 17, 1976

Related U.S. Application Data

[60] Division of Ser. No. 609,998, Sep. 3, 1975, Pat. No. 4,016,202, which is a continuation-in-part of Ser. No. 444,713, Feb. 22, 1974, Pat. No. 3,925,446.

[30] Foreign Application Priority Data

Feb. 28, 1973 Germany .............................. 2309887
Jan. 26, 1974 Germany .............................. 2403809

[51] Int. Cl.² ...................................... A61K 31/135
[52] U.S. Cl. ........................................... 424/330
[58] Field of Search ................................ 424/330

[56] References Cited

U.S. PATENT DOCUMENTS

| 3,459,782 | 8/1969 | Koppe et al. | 260/465 |
| 3,541,130 | 11/1970 | Koppe et al. | 260/465 |
| 3,712,927 | 1/1973 | Howe et al. | 260/465 |

*Primary Examiner*—Stanley J. Friedman
*Attorney, Agent, or Firm*—Hammond & Littell

[57] ABSTRACT

Pharmaceutical dosage unit compositions containing as an active ingredient a 1-aryloxy-2-hydroxy-3-alkynylamino-propane selected from the group consisting of racemic or optically active compounds of the formula

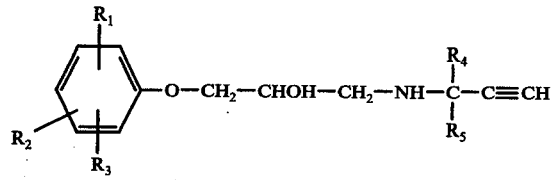

wherein
$R_1$ is a member selected from the group consisting of hydrogen; halogen; nitro; alkyl having from 1 to 5 carbon atoms; alkoxy having from 1 to 4 carbon atoms; alkenyl having from 2 to 5 carbon atoms; alkynyl having from 2 to 5 carbon atoms; alkylamino having from 1 to 5 carbon atoms; dialkylamino having from 1 to 5 carbon atoms in each alkyl; alkoxyalkyl having from 2 to 6 carbon atoms; alkylaminoalkyl having from 2 to 6 carbon atoms; dialkylaminoalkyl having from 3 to 12 carbon atoms; $-(CH_2)_x-NH_2$ or $-(CH_2)_x-OH$, where $x$ is an integer from 0 to 3; alkynyloxy having from 3 to 6 carbon atoms; alkenyloxy having from 3 to 6 carbon atoms; $-CO-R_9$, where $R_9$ is a member selected from the group consisting of alkyl having 1 to 6 carbon atoms, phenylalkyl having 7 to 10 carbon atoms and phenyl; cycloalkyl having from 3 to 7 carbon atoms; phenyl; phenyl substituted with a substituent selected from the group consisting of halogen, lower alkyl, lower alkoxy and nitro; phenoxy; and phenoxy substituted with a substituent selected from the group consisting of halogen, lower alkyl, lower alkoxy and nitro;

$R_2$ is a member selected from the group consisting of hydrogen, halogen, alkyl having from 1 to 4 carbon atoms, alkoxy having from 1 to 4 carbon atoms, alkanoyl having from 2 to 4 carbon atoms, alkenyl having from 2 to 4 carbon atoms, amino and nitro;

$R_3$ is a member selected from the group consisting of hydrogen, halogen, alkyl having from 1 to 4 carbon atoms, alkoxy having from 1 to 4 carbon atoms and, together with $R_2$ in the ortho-position, $-CH=CH-CH=CH-$ or $-(CH_2)_n-$, where $n$ is an integer from 3 to 5;

$R_4$ is a member selected from the group consisting of hydrogen and alkyl having from 1 to 3 carbon atoms; and $R_5$ is a member selected from the group consisting of alkyl having from 1 to 3 carbon atoms, and, together with $R_4$, $-(CH_2)_p-$, where $p$ is an integer from 4 to 6;

and physiologically compatible acid addition salts thereof; and a method of using the same as adrenolytics and hypotensives.

30 Claims, No Drawings

PHARMACEUTICAL COMPOSITIONS CONTAINING A 1-PHENOXY-2-HYDROXY-3-ALKYNYLAMINO-PROPANE AND METHOD OF USE

This is a division of copending application Ser. No. 609,998 filed Sept. 3, 1975, now U.S. Pat. No. 4,016,202 granted Apr. 5, 1977 which in turn is a continuation-in-part of application Ser. No. 444,713 filed Feb. 22, 1974, now U.S. Pat. 3,925,446 granted Dec. 9, 1975.

This invention relates to novel pharmaceutical compositions containing 1-aryloxy-2-hydroxy-3-alkynylamino-propanes or physiologically compatible acid addition salts thereof and to methods of using the same as adrenolytics and hypotensives.

More particularly, this invention relates to novel pharmaceutical compositions containing a 1-aryloxy-2-hydroxy-3-alkynylamino-propane selected from the group consisting of racemic or optically active compounds of the formula

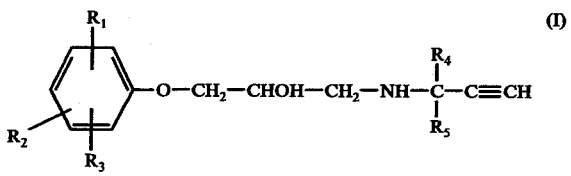

wherein
$R_1$ is a member selected from the group consisting of hydrogen, halogen, nitro; alkyl having from 1 to 5 carbon atoms; alkoxy having from 1 to 4 carbon atoms; alkenyl having from 2 to 5 carbon atoms; alkynyl having from 2 to 5 carbon atoms; alkylamino having from 1 to 5 carbon atoms; dialkylamino having from 1 to 5 carbon atoms in each alkyl; alkoxyalkyl having from 2 to 6 carbon atoms; alkylaminoalkyl having from 2 to 6 carbon atoms; dialkylaminoalkyl having from 3 to 12 carbon atoms; $-(CH_2)_x-NH_2$ or $-(CH_2)_x-OH$, where $x$ is an integer from 0 to 3; alkynyloxy having from 3 to 6 carbon atoms; alkenyloxy having from 3 to 6 carbon atoms; $-CO-R_9$, where $R_9$ is a member selected from the group consisting of alkyl having 1 to 6 carbon atoms, phenylalkyl having from 7 to 10 carbon atoms and phenyl; cycloalkyl having from 3 to 7 carbon atoms; phenyl; phenyl substituted with a substituent selected from the group consisting of halogen, lower alkyl, lower alkoxy and nitro; phenoxy; and phenoxy substituted with a substituent selected from the group consisting of halogen, lower alkyl, lower alkoxy and nitro;
$R_2$ is a member selected from the group consisting of hydrogen, halogen, alkyl having from 1 to 4 carbon atoms, alkoxy having from 1 to 4 carbon atoms, alkanoyl having from 2 to 4 carbon atoms, alkenyl having from 2 to 4 carbon atoms, amino and nitro;
$R_3$ is a member selected from the group consisting of hydrogen, halogen, alkyl having from 1 to 4 carbon atoms, alkoxy having from 1 to 4 carbon atoms and, together with $R_2$ in the ortho-position, $-CH=CH-CH=CH-$ or $-(CH_2)_n-$, where $n$ is an integer from 3 to 5;
$R_4$ is a member selected from the group consisting of hydrogen and alkyl having from 1 to 3 carbon atoms; and
$R_5$ is a member selected from the group consisting of alkyl having from 1 to 3 carbon atoms, and, together with $R_4$, $-(CH_2)_p-$, where $p$ is an integer from 4 to 6;

and physiologically compatible acid addition salts thereof.

If $R_1$ represents a lower aliphatic acyl group, lower alkanoyl, such as the acetyl, propionyl, butyryl or isobutyryl group, may, for example, be considered here. As an araliphatic acyl group, $R_1$ may represent phenylalkanoyl, such as the phenacetyl group, which is optionally substituted at the phenyl with one or several halogen atoms, alkyl groups, nitro, cyano or carboxyl group. If $R_1$ represents aromatic acyl, it may be, for example, a benzoyl group optionally substituted once or several times by halogen, lower alkyl, nitro, cyano or carboxyl.

If $R_1$ represents an acyloxy or acylamino group, the acyl group therein may as well be represented by the acyl groups individually listed in the above paragraph.

The compounds embraced by formula I may be produced in a number of ways, of which the following are representative:

(a) Reacting a compound of the formula

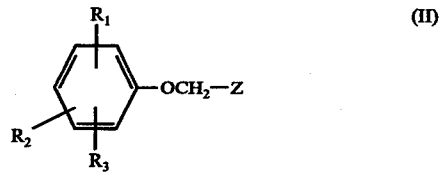

where $R_1$ to $R_3$ are defined as in formula I and Z is

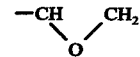

or $-CHOH-CH_2-Hal$ (Hal = halogen), with an amine of the formula

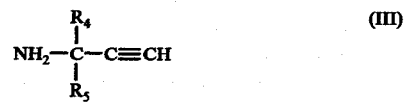

where $R_4$ and $R_5$ have the meanings indicated in formula I;

(b) Cleaving an easily removable protective group off compounds of the formula

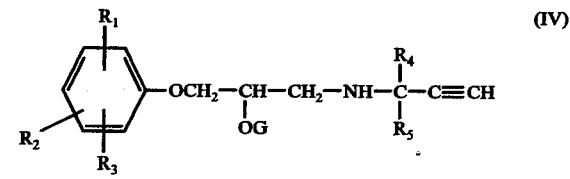

where $R_1$ to $R_5$ are defined as in formula I and G is an easily hydrogenolytically removable, group, for example, an acyl or an acetal group.

(c) Cleaving a protective group off a compound of the formula

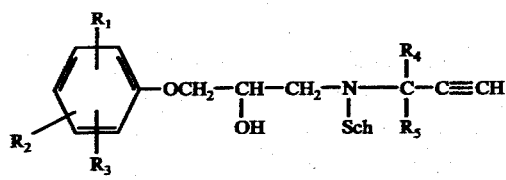

(V)

where $R_1$ to $R_5$ are defined as in formula I and Sch is an easily removable protective group, for example, an acyl group or the carbobenzoxy group;

(d) Hydrolyzing an oxazolidine derivative of the formula

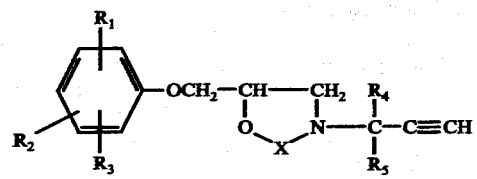

(VI)

where $R_1$ to $R_5$ are defined as in formula I, and X represents —CO—, —$CH_2$— or a —CH—lower alkyl group, for example, with sodium hydroxide or potassium hydroxide solution in water or in an alcohol/water mixture.

In addition, other processes for the production of compounds of formula I are possible, such as converting a compound already having the 3-alkynylaminopropanol-2 side chain, but not having one of the substituents $R_1$, $R_2$ or $R_3$ on the phenyl ring and in place thereof another substituent convertible to the desired substituent $R_1$, $R_2$ or $R_3$ by conventional methods.

(e) Converting compounds of the formula

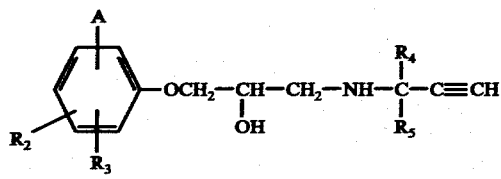

(VIIa)

where $R_2$ to $R_5$ are defined as in formula I and A is a group convertible by conventional methods, such as the —$CONH_2$ or —$COOR_6$ group (where $R_6$ is defined as in formula I), an alkoxy, O-acyl or $NO_2$ group, or compounds of the formula

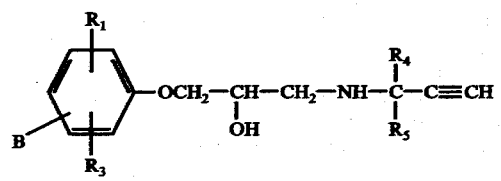

(VIIb)

where $R_1$ and $R_3$ to $R_5$ are defined as in formula I and B is a group convertible into $R_2$ by conventional methods, into compounds of the formula I, using the method required in each case (splitting off water, reducing, saponifying, cleaving an ether, alkylating).

Furthermore, the following process is suitable for producing compounds of the formula I, where $R_2$ or $R_3$ is a halogen atom:

(f) Introducing a halogen atom into compounds of the formula

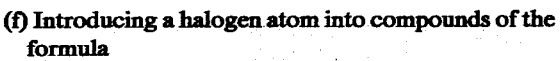

(VIII)

where $R_4$ and $R_5$ are defined as in formula I, and Ar is a group of the partial formula

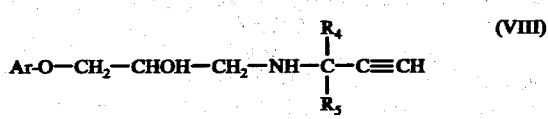

(where $R_1$, $R_2$ and $R_3$ have the above meanings), for example, with a mixture of a hydrogen halide and hydrogen peroxide at elevated temperature.

Some of the starting compounds required for carrying out the processes (a) to (f) are known. The remainder can be obtained by known processes. Thus, the epoxides of the formula II may be produced easily by reaction with a corresponding phenol or phenolate of the formula

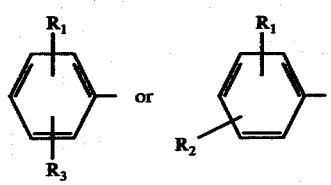

(X)

where $R_1$ to $R_3$ have the meanings mentioned above and Kt is hydrogen or a cation (e.g., an alkali metal cation). The epoxides may be used for production of further starting materials; for instance, the halohydrins of the formula II may be produced by reacting the epoxides with the corresponding hydrogen halide.

Amines of the formula III are known and represent mostly commercial products. Compounds of the formula IV may be obtained by reacting a halohydrin of the formula II with a compound (such as vinyl ether or dihydropyran) to give the protective group G and, subsequently, reacting the obtained compound of the formula

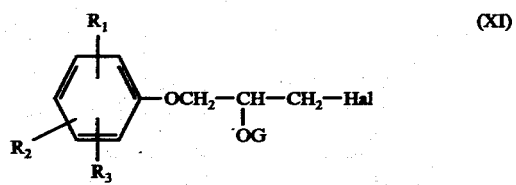

(XI)

with a compound of the formula III.

The tertiary amines of the formula V are obtained by reacting a compound of the formula X with a compound of the formula

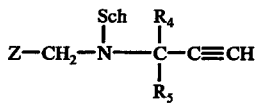

where $R_4$, $R_5$ and Sch have the above-mentioned meanings and Z is halogen.

The oxazolidinones of the formula VI (e.g., compounds where X = CO) are producible, for example, starting from the epoxides of the formula II, by reacting the latter with a urethane (producible from a chloroethyl formate and an amine of the formula II) of the formula

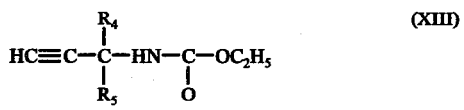

where $R_4$ and $R_5$ have the meanings mentioned above.

The compounds of the formulas VIIa, VIIb and VIII already contain the complete 1-phenoxy-2-hydroxy-3-alkynyl-amino-propane structure and may, therefore, be produced analogous to process (a) described above, starting from the corresponding phenol, via the corresponding 1-phenoxy-2,3-epoxy-propane (producible by reaction with epichlorohydrin) by reaction with an alkynylamine of the formula III.

The compounds of the formula I possess an asymmetric carbon atom at the CHOH group and can occur, therefore, as racemates as well as in the form of optical antipodes. The latter may be obtained by separation of racemates with the conventional optically active acids, such as dibenzoyl- (or di-p-toluyl-)D-tartaric acid or D-3-bromocamphor-8-sulfonic acid or by using optically active starting materials as well.

The 1-aryloxy-2-hydroxy-3-alkynylamino-propanes of the formula I may be converted into physiologically compatible acid addition salts thereof in the conventional way. Suitable acids are, for example, hydrochloric acid, hydrobromic acid, sulfuric acid, methane-sulfonic acid, maleic acid, acetic acid, oxalic acid, lactic acid, tartaric acid or 8-chlorotheophylline.

The compounds of the formula I and the physiologically compatible acid addition salts thereof have shown valuable therapeutic properties, in particular, adrenolytic properties as demonstrated by animal tests in guinea pigs and may, therefore, be used for treatment or prophylaxis of diseases of the coronaries and for treatment of cardiac arrhythmia, especially of tachycardia, in human medicine. The blood-pressure decreasing properties of the compounds are therapeutically interesting too. Compared to the known β-receptor blockers, for example, the commerical product 1-(1-naphthyloxy)-2-hydroxy-3-isopropylaminopropane (Propranolol), the compounds have the advantage of a considerably decreased toxicity combined with a superior action.

The invention, therefore, also relates to a process for the treatment of coronary diseases, cardiac arrhythmia and high blood pressure in warm-blooded animals comprising administering a safe but effective amount of a 1-aryloxy-2-hydroxy-3-alkynylamino-propane compound of the formula I.

Here, compounds of the formula I have proved to be valuable, in particular, where $R_4$ and $R_5$ represent each a methyl group and one of $R_1$, $R_2$ and $R_3$ is other than hydrogen (substituted 1-phenoxy-3-(2-methylbutynyl-3-amino-2)-2-propanols).

Among the preferred meanings for $R_1$ are to be stressed the unsaturated substituents such as alkenyl (e.g., allyl), alkynyl (e.g., ethynyl, propynyl), alkenyloxy (e.g., allyloxy) or alkynyloxy (e.g., propargyloxy) in particular, if they stand in the 2-position to the propanolamine side-chain.

$R_2$ may represent in this case preferably hydrogen, but furthermore, lower alkyl (e.g., methyl), preferably in the 5-position to the propanolamine side-chain, while $R_3$ is hydrogen as a rule. $R_4$ and $R_5$ are again preferably methyl.

A further preferred sub-group is formed by those compounds of the formula I, where $R_1$ represents a hydroxyalkyl, in particular, the hydroxymethyl group; or an amino or acylamino, especially acetylamino group; whereby $R_2$ and $R_3$ may represent in the first case hydrogen, in the second case hydrogen or else halogen or lower alkyl. $R_4$ and $R_5$ are again preferably methyl.

Important individual compounds are, in particular: 1-(2-ethynylphenoxy)-3-(2-methylbutynyl-3-amino-2)-2-propanol, 1-(2-allylphenoxy)-3-(2-methylbutynyl-3-amino-2)-2-propanol, furthermore, 1-(3,5-dibromo-4-aminophenoxy)-3-(2-methylbutynyl-3-amino-2)-2-propanol, 1-(2-hydroxymethyl-phenoxy)-2-(2-methylbutynyl-3-amino-2)-2-propanol, the 1-(3-chlorophenoxy)-3-(2-methylbutynyl-3-amino-2)-2-propanol and the 1-(4-acetamidophenoxy)-3-(2-methylbutynyl-3-amino-2)-2-propanol or the physiologically compatible acid addition salts thereof.

The single dose of the compounds lies at 1 to 300 mgm, preferably 5 to 100 mgm (orally) or 1 to 20 mgm (parenterally). When administered to warm-blooded animals, the single dosage range is from 0.015 to 5 mgm/kg.

The active ingredients according to the invention may be incorporated into the conventional galenic forms of administration, such as tablets, coated tablets, solutions, emulsions, powders, capsules or forms of sustained release. For the production of the above, the usual pharmaceutical excipients as well as the conventional methods of production may be applied.

Corresponding tablets may be obtained by mixing the active ingredients with known excipients, for example, with inert diluents, such as calcium carbonate, calcium phosphate or lactose, disintegrants, such as corn starch or alginic acid, binders, such as starch or gelatin, lubricants, such as magnesium stearate or talc and/or agents for obtaining sustained release, such as carboxypolymethylene, carboxymethylcellulose, cellulose acetate/phthalate or polyvinylacetate.

The tablets may also be composed of several layers. There may be produced correspondingly coated tablets by means of coating cores, prepared analogous to the tablets, with agents usually applied for tablet-coats, such as polyvinylpyrrolidone or shellac, gum arabic, talcum, titanium dioxide or sugar. For obtaining sustained release or in order to avoid incompatibilities, the core may consist of several layers as well. Thus, the tablet coat for obtaining sustained release may also consist of several layers, where the excipients mentioned above for tablets may be used.

Potable solutions of the active ingredients or active ingredient combinations according to the invention may additionally contain a sweetener, such as saccharin, cyclamate, glycerin or sugar, as well as an agent improving the taste, for example, a flavor, such as vanilla or orange extract. Besides, they may comprise suspension auxiliaries or thickeners, such as sodium carboxymethylcellulose, wetting agents, such as condensation products of fatty alcohols with ethylene oxide, or preservatives, such as p-hydroxybenzoates.

Injectable solutions are produced in the conventional way, such as under addition of preservation agents, such as p-hydroxybenzoates, or stabilizers, such as "Komplexonen" (the sodium salt of ethylene diaminetetraacetic acid), and filed into injection vials or ampules.

Capsules containing the active ingredients or active ingredient combinations may be produced, for example, by admixing the active ingredients with inert carriers, such as lactose or sorbitol, and filling same into gelatin capsules.

Suitable suppositories may be produced by mixing the active ingredients or active ingredient combinations envisaged for same with conventional carriers, such as neutral fats or polyoxyethyleneglycol or its derivatives.

The active ingredients of the invention are suitable as well for combination with other pharmacodynamically active substances, such as for example, coronary dilators, sympathicomimetics, cardiac glycosides or tranquilizers.

The following examples illustrate the preparation of compounds of the formula I and physiologically compatible acid addition salts thereof.

EXAMPLE 1

1-α-Naphthoxy-3-(3-ethylpentynyl-4-amino-3)-2-propanol . HCl (according to process [a]) (I, $R_1 = H$, $R_2 + R_3 = -CH=CH-CH=CH-$, $R_4$ and $R_5 = C_2H_5$).

10 Grams (0.05 mol) of 1-α-naphthoxy-2,3-epoxypropane were dissolved in 80 ml of ethanol. 5.55 Grams (0.05 mol) of 3-ethyl-3-amine-pentyne-4 were added and the mixture was refluxed for two hours at boiling temperature. After having cooled off, the solvent was distilled off. The residue was dissolved in ether and acidified with alcoholic HCl. The crystallizable compound was isolated and recrystallized from a mixture of acetonitrile and ethanol. Yield: 9.5 gm, m.p. 195°–196° C.

EXAMPLE 2

1-m-Tolyloxy-3-(2-methylbutynyl-3-amino-2)-2-propanol . HCl (according to process [a]) (I, $R_1 = $ 3-$CH_3$, $R_2$ and $R_3 = H$, $R_4$ and $R_5 = CH_3$).

8.2 gm (0.05 mol) of 1-m-tolyloxy-2,3-epoxypropane were dissolved in 90 ml of ethanol, and after addition of 6.25 gm (0.075 mol) of 2-methyl-2-aminobutyne-3, the mixture was refluxed for two hours. After distilling off the solvent, the residue was recrystallized from ethyl acetate under addition of petroleum ether. The crystalline base was dissolved in acetonitrile; alcoholic HCl was added and crystallization was started under addition of ether. 6.5 gm of colorless crystals were obtained, which are chromatographically pure. M.p. 139°–141° C.

EXAMPLE 3

1-(2-Allylphenoxy)-3-(2-methylbutynyl-3-amino-2)-2-propanol oxalate (according to process [a]) (I, $R_1 = $ 2-allyl, $R_2$ and $R_3 = H$, $R_4$ and $R_5 = CH_3$).

9.5 gm (0.05 mol) of 1-(2-allylphenoxy)-2,3-epoxypropane were dissolved in 60 ml of methanol. 8.3 gm (0.1 mol) of 2-metyl-2-amino-butyne-3 were added and the mixture was refluxed for three hours. After having distilled off the solvent, the basic residue was dissolved in acetone and a solution of 6 gm of oxalic acid was added. The precipitating crystalline oxalate was recrystallized from acetone once more. Yield: 4.7 gm, m.p. 144°–146° C.

Analogous to the Examples 1 to 3, the following compounds of the formula I were prepared by process (a), i.e. by reacting the correspondingly substituted 1-phenoxy-2,3-epoxypropane of the formula II with the corresponding amine of the formula III in ethanol.

TABLE

| $R_1$ | $R_2$ | $R_3$ | $R_4$ | $R_5$ | M.P. of HCl-salt in case nothing else indicated °C |
|---|---|---|---|---|---|
| 3-$CH_3$ | H | H | $C_2H_5$ | $C_2H_5$ | 143–145 |
| 2-O—$CH_2$—CH=$CH_2$ | H | H | $C_2H_5$ | $C_2H_5$ | 112–113 |
| 2-$CH_2$—CH=$CH_2$ | H | H | $C_2H_5$ | $C_2H_5$ | 128–129 |
| H | | 2,3-CH=CH—CH=CH— | $CH_3$ | $CH_3$ | 159–161 |
| 2-O—$CH_2$—CH=$CH_2$ | H | H | $CH_3$ | $CH_3$ | 100–103 |
| 3-$CH_3$ | H | H | —($CH_2$)$_5$— | | 159–160 |
| 2-$CH_2$—CH=$CH_2$ | H | H | —($CH_2$)$_5$— | | 120–122 |
| 2-Br | H | H | $CH_3$ | $CH_3$ | 138–139 |
| 4-$NO_2$ | H | H | $CH_3$ | $CH_3$ | 183–184 |
| 4-$CH_2OH$ | H | H | $CH_3$ | $CH_3$ | 108–110 (Base) |
| 2-$OCH_3$ | H | H | $CH_3$ | $CH_3$ | 161–163 |
| 4-$COOCH_3$ | H | H | $CH_3$ | $CH_3$ | 127–129 |
| H | | 3,4-($CH_2$)$_3$— | $CH_3$ | $CH_3$ | 139–140 |
| 4-tert.$C_4H_9$ | H | H | $CH_3$ | $CH_3$ | 146–147 |
| 2-iso $C_3H_7$ | H | H | $CH_3$ | $CH_3$ | 157–158 |
| 2-C≡CH | H | H | $CH_3$ | $CH_3$ | 165–167 |
| 4-NH—CO—$NHCH_3$ | H | H | $CH_3$ | $CH_3$ | 107–109 (Base) |
| 4-NH—CO—N($C_2H_5$)$_2$ | H | H | $CH_3$ | $CH_3$ | 125–127 |
| 4-$CH_2$—CO—$NH_2$ | H | H | $CH_3$ | $CH_3$ | 107–110 (Base) |
| 3-($C_2H_5$)$_2$N— | H | H | $CH_3$ | $CH_3$ | 134–137 (dihydrochloride) |
| 4-COOH | H | H | $CH_3$ | $CH_3$ | 159–162 |
| 4-NH—$COCH_3$ | H | H | $CH_3$ | $CH_3$ | 137–138 (Base) |
| 2-$CH_2OH$ | H | H | $CH_3$ | $CH_3$ | 150–152 (oxalate) |
| 2-$C_6H_{11}$ | H | H | $CH_3$ | $CH_3$ | 150–152 |
| 2-Cl | 4-Cl | H | $CH_3$ | $CH_3$ | 170–171 |

TABLE-continued

| $R_1$ | $R_2$ | $R_3$ | $R_4$ | $R_5$ | M.P. of HCl-salt in case nothing else indicated °C |
|---|---|---|---|---|---|
| 3-Cl | H | H | $CH_3$ | $CH_3$ | 142–144 |
| 2-$CONH_2$ | H | H | $CH_3$ | $CH_3$ | 230–233 |
| 3-Br | 4-$NH_2$ | 5-Br | $CH_3$ | $CH_3$ | 183–185 (dihydrochloride) |
| 2-C≡C—$CH_3$ | H | H | $CH_3$ | $CH_3$ | 164–166 |
| H | | 3,4-O—$(CH_2)$—O— | $CH_3$ | $CH_3$ | 175–176 |
| 4-CO—$C_2H_5$ | H | H | $CH_3$ | $CH_3$ | 149–151 |
| 4-OH | H | H | $CH_3$ | $CH_3$ | 136–137.5 (Base) |
| 2-$C_6H_5$ | H | H | $CH_3$ | $CH_3$ | 157–158 |
| 2-Cl | H | H | $CH_3$ | $CH_3$ | 150–151 |

EXAMPLE 4

1-(2-Allyloxyphenoxy)-3-(2-methylbutynyl)-3-amino-2)-2-propanol . HCl (according to process [b]) (I, $R_1 =$ 2-$OCH_2CH=CH_2$, $R_2$ and $R_3 =$ H, $R_4$ and $R_5 = CH_3$).

2.4 gm (0.025 mol) of tetrahydropyran were dropped slowly into 6.42 gm (0.025 mol) of 1-(2-allyloxyphenoxy)-3-bromo-2-propanol and a catalytical quantity of p-toluene-sulfonic acid at 20°–25° C. Then the mixture was heated for 30 minutes to 40° C, dissolved in 40 ml of benzene, and 5 gm (0.06 mol) of 2-methyl-2-aminebutyne-3 were added to it. The mixture was refluxed for two hours; then the solvent was distilled off and the residue was heated for 15 minutes with dilute hydrochloric acid to 80° C. After cooling off, it was extracted from ether and the aqueous phase was made alkaline by NaOH. The precipitating basic portions were taken up in ether. The organic phase was dried with $MgSO_4$ and after filtering the ether was distilled off. The residue was dissolved in little ethanol. EthericHCl was added and the crystalline hydrochloride recrystallized twice. M.p. 99°–102° C.

EXAMPLE 5

1-(4-Nitrophenoxy)-3-(2-methylbutynyl-3-amino-2)-2-propanol . HCl (according to process [c]) (I, $R_1 =$ 4-$NO_2$, $R_2$ and $R_3 =$ H, $R_4$ and $R_5 = CH_3$).

2.7 gm (approximately 0.008 mol) of 1-(4-nitrophenoxy)-3-(N-acetyl-2-methylbutynyl-3-amino-2)-2-propanol were refluxed in 25 ml of ethanol with 1 gm of KOH for two hours. After having distilled off the solvent, a viscous residue remained, which was treated with diluted HCl. After shaking out with chloroform, the aqueous phase was made alkaline with NaOH and the precipitating amine was taken up in chloroform. After drying over $NaSO_4$, the solvent was distilled off and the residue was recrystallized from ethyl acetate under addition of petroleum ether. Yield: 1.5 gm, m.p. 125°–127° C (base). Mixed melting point with substance obtained according to process (a) : 126°–127° C.

EXAMPLE 6

1-(4-Aminophenoxy)-3-(2-methylbutynyl-3-amino-2)-2-propanol . HCl (according to process [e]) (I, $R_1 =$ 4-$NH_2$, $R_2$ and $R_3 =$ H, $R_4$ and $R_5 = CH_3$).

A mixture of 8.1 gm of tin-II chloride in 20 ml of concentrated HCl was heated to 60° C and 2.62 gm (0.01 mol) of 1-(4-nitrophenoxy)-3-(2-methylbutynyl-3-amino-2)-2-propanol were added in portions, so that the temperature did not exceed 65° C. After the addition has been finished, the mixture was stirred for 30 minutes and after cooling off it was adjusted alkaline with NaOH. The precipitating basic portions were shaken with chloroform. The chloroform solution was washed with water and dried over $Na_2SO_4$. After distilling off the $CHCl_3$, a solid residue remained, which was recrystallized from ethyl acetate under addition of petroleum ether. Yield: 1.4 gm, m.p. 122°–123° C (base).

According to process (e), the compound 1-(4-hydroxyphenoxy)-3-(2-methylbutynyl-3-amino-2)-2-propanol was made by heating the compound 1-(4-diethylaminocarbonyloxyphenoxy)-3-(2-methylbutynyl-3-amino-2)-2-propanol (m.p. of hydrochloride: 126° C) in the presence of concentration aqueous HCl. M.p. of the end product (base) is 136°–137.5° C.

EXAMPLE 7

1-(4-Hydroxycarbonylphenoxy)-3-(2-methylbutynyl-3-amino-2)-2-propanol . HCl (according to process [e]) (I, $R_1 = R-COOH$, $R_2$ and $R_3 =$ H, $R_4$ and $R_5 = CH_3$).

5 gm of 1-(4-ethoxycarbonylphenoxy)-3-(2-methylbutynyl-3-amino-2)-2-propanol hydrochloride were refluxed in 30 ml of concentrated HCl for two hours. After cooling, the crystalline mass that originated by hydrolysis was vacuum filtered and recrystallized twice from ethanol under addition of ether. Yield: 3.1 gm, m.p. 159°–162° C.

EXAMPLE 8

1-(3,5-Dibromo-4-aminophenoxy)-3-(2-methylbutynyl-3-amino-2)-2-propanol . 2 HCl (according to process [f]) (I, $R_1 =$ 4-$NH_2$, $R_2 =$ 3-Br, $R_3 =$ 5-Br, $R_4$ and $R_5 = CH_3$).

4.96 gm (0.02 mol) of 1-(4-aminophenoxy)-3-(2-methylbutynyl-3-amino-2)-2-propanol were added into a mixture of 30 ml of HBr (65%) and 10 ml of water and heated to 45° C. While stirring and cooling, 4.54 gm (0.04 mol) of $H_2O_2$, 30%, were dropped into the mixture in such a way that the temperature did not rise over 65° C. After it has been kept at approximately 65° C for a further 30 minutes, the crystalline substance was vacuum filtered after cooling. It was then recrystallized from ethanol under addition of ether. Then the hydrochloride was dissolved in water. NaOH was added. The base was extracted with $CHCl_3$ and, after evaporation of the solvent, recrystallized from ethyl acetate under addition of petroleum ether. The chromatographically pure base was dissolved in ethanol; alcoholic HCl was added and the dihydrochloride was brought to crystallization under addition of ether. Yield: 3.8 gm, m.p. 183°–185° C.

EXAMPLES OF FORMULATIONS

1. Tablets

| | | |
|---|---|---|
| 1-(4-aminophenoxy)-3-(2-methylbutynyl-3-amino-2-)-2-propanol . HCl | | 40.0 parts |
| Corn starch | | 164.0 parts |
| Secondary calcium phosphate | | 240.0 parts |
| Magnesium stearate | | 1.0 parts |
| | Total | 445.0 parts |

Production:
The individual components were admixed well and the mixture was granulated in the usual way. The granulate was pressed into tablets of 445 mgm by weight, of which each contains 40 mgm of active ingredient.

2. Gelatin capsules

The content of the capsules was composed as follows:

| | | |
|---|---|---|
| 1-(2-ethynylphenoxy)-3-(2-methylbutynyl-3-amino-2-)-2-propanol . HCl | | 25.0 parts |
| Corn starch | | 175.0 parts |
| | Total | 200.0 parts |

Production:
The active ingredients of the content of capsule were mixed well and 200 mgm portions of the mixture were filled into gelatin capsules of suitable size. Each capsule contains 25 mgm of the active ingredient.

3. Injection Solution

The solution was produced of the following ingredients:

| | |
|---|---|
| 1-(2-allylphenoxy)-3-(2-methylbutynyl-3-amino-2-)-2-propanol . HCl | 2.5 parts |
| Sodium salt of EDTA (ethylenediamine-tetraacetic acid) | 0.2 parts |
| Distilled water ad | 100.0 parts |

Production:
The active ingredient and EDTA-salt were dissolved in sufficient water and filled with water to the desired volume. The solution was filtered free from suspended particles and filled into ampules under aseptic conditions. Finally, the ampules were sterilized and sealed. Each ampule contains 25 mgm of active ingredient.
Instead of the active ingredient mentioned in this example, 1-(2-hydroxymethylphenoxy)-3-(2-methylbutynyl-3-amino-2)-2-propanol . HCl in the same quantity may be used as well.

4. Coated Tablets with Sustained Release

| | | |
|---|---|---|
| Core: | | |
| (-)-1-(4-aminophenoxy)-3-(2-methylbutynyl-3-amino-2-)-2-propanol . HCl | | 25.0 parts |
| Carboxymethyl cellulose (CMC) | | 295.0 parts |
| Stearic acid | | 20.0 parts |
| Cellulose acetate/phthalate (CAP) | | 40.0 parts |
| | Total | 380.0 parts |

Production:
Active ingredient, CMC and stearic acid were mixed well and the mixture was granulated in the usual way, using a solution of the CAP in 200 ml of a mixture of ethanol/ethyl acetate. Then the granulate was pressed to 380 mgm cores, coated in the conventional way with a sugary 5% solution of polyvinylpyrrolidone in water. Each tablet contains 25 mgm of active ingredient.

5. Tablets

| | | |
|---|---|---|
| 1-α-Naphthoxy-3-(3-ethylpentynyl-4-amino-3-)-2-propanol . HCl | | 35.0 gm |
| 2,6-bis-(diethanolamino)-4,8-dipiperidinopyrimido-[5,4-d]-pyrimidine | | 75.0 gm |
| Lactose | | 164.0 gm |
| Corn starch | | 194.0 gm |
| Colloidal silicic acid | | 14.0 gm |
| Polyvinylpyrrolidone | | 6.0 gm |
| Magnesium stearate | | 2.0 gm |
| Soluble starch | | 10.0 gm |
| | Total | 500.0 gm |

Instead of the β-adrenolytically active substances mentioned in this example, the substances 1-(2-allyloxyphenoxy)-3-(2-methylbutynyl-3-amino-2-propanol . HCl and 1-(2-propargyloxyphenoxy)-3-(2-methylbutynyl-3-amino-2)-2-propanol . HCl may be used as well in the same quantity.

Production:
The active ingredient together with the lactose, corn starch, colloidal silicic acid and polyvinyl pyrrolidone was granulated after thorough mixing in the usual way, using an aqueous solution of the soluble starch. The granulate was admixed with the magnesium stearate and pressed into 1000 tablets each of 500 mgm of weight, containing each 35 mgm of the first and 75 mgm of the second active ingredient.

The preceding specific embodiments are illustrative of the practice of the invention. It is to be understood, however, that other expedients known to those skilled in the art or disclosed herein may be employed without departing from the spirit of the invention and the scope of the appended claims.

We claim:
1. A pharmaceutical dosage unit composition consisting essentially of an inert pharmaceutical carrier and an effective adrenolytic or hypotensive amount of a 1-aryloxy-2-hydroxy-3-alkynylamino-propane selected from the group consisting of racemic or optically active compounds of the formula

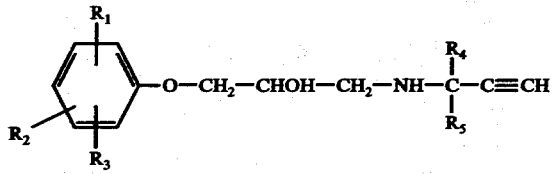

wherein
$R_1$ is a member selected from the group consisting of hydrogen; halogen; nitro; alkyl having from 1 to 5 carbon atoms; alkoxy having from 1 to 4 carbon atoms; alkenyl having from 2 to 5 carbon atoms; alkynyl having from 2 to 5 carbon atoms; alkylamino having from 1 to 5 carbon atoms; dialkylamino having from 1 to 5 carbon atoms in each alkyl; alkoxyalkyl having from 2 to 6 carbon atoms; alkylaminoalkyl having from 2 to 6 carbon atoms; dialkylaminoalkyl having from 3 to 12 carbon atoms; —$(CH_2)_x$—$NH_2$ or —$(CH_2)_x$—OH, where $x$ is an integer from 0 to 3; alkynyloxy having from 3 to 6 carbon atoms; alkenyloxy having from 3 to 6 carbon atoms; —CO—$R_9$, where $R_9$ is a member selected from the group consisting of alkyl having 17. The method of claim 16, where $R_4$ and $R_5$ are methyl, and $R_1$, $R_2$ and $R_3$ have the meanings defined in claim 16.

18. The method of claim 16, where $R_1$ is a member selected from the group consisting of alkenyl having from 2 to 5 carbon atoms, alkynyl having from 2 to 5 carbon atoms, alkenyloxy having from 3 to 6 carbon atoms and alkynyloxy having from 3 to 6 carbon atoms; $R_2$ and $R_3$ are members selected from the group consisting of hydrogen and alkyl having from 1 to 4 carbon atoms, and $R_4$ and $R_5$ have the meanings defined in claim 16.

19. The method of claim 18, where $R_4$ and $R_5$ are methyl.

20. The method of claim 16, where $R_1$ is a member selected from the group consisting of allyl, ethynyl, propynyl, allyloxy and propargyloxy, $R_2$ and $R_3$ are hydrogen and $R_4$ and $R_5$ are methyl.

21. The method of claim 20, where $R_1$ is in the 2-position to the propanolamine side chain.

22. The method of claim 16, where $R_1$ is hydroxyalkyl having from 1 to 3 carbon atoms, $R_2$ and $R_3$ are hydrogen and $R_4$ and $R_5$ have the meanings defined in claim 16.

23. The method of claim 22, where $R_1$ is hydroxymethyl.

24. The method of claim 22, where $R_4$ and $R_5$ are methyl.

25. The method of claim 16, where $R_1$ is amino, $R_2$ and $R_3$ are members selected from the group consisting of hydrogen, halogen and alkyl having from 1 to 4 carbon atoms, and $R_4$ and $R_5$ have the meanings defined in claim 16.

26. The method of claim 16, where $R_1$ is 3-ethynyl, $R_2$ and $R_3$ are hydrogen and $R_4$ and $R_5$ are methyl.

27. The method of claim 16, where $R_1$ is 2-allkl, $R_2$ and $R_3$ are hydrogen and $R_4$ and $R_5$ are methyl.

28. The method of claim 16, where $R_1$ is 4-amino, $R_2$ is 3-bromo, $R_3$ is 5-bromo and $R_4$ and $R_5$ are methyl.

29. The method of claim 16, where $R_1$ is 2-hydroxymethyl, $R_2$ and $R_3$ are hydrogen and $R_4$ and $R_5$ are methyl.

30. The method of claim 16, where $R_1$ is 3-chloro, $R_2$ and $R_3$ are hydrogen and $R_4$ and $R_5$ are methyl.

* * * * *

1 to 6 carbon atoms, phenylalkyl having 7 to 10 carbon atoms and phenyl; cycloalkyl having from 3 to 7 carbon atoms; phenyl; phenyl substituted with a substituent selected from the group consisting of halogen, lower alkyl, lower alkoxy and nitro; phenoxy; and phenoxy substituted with a substituent selected from the group consisting of halogen, lower alkyl, lower alkoxy and nitro;

$R_2$ is a member selected from the group consisting of hydrogen, halogen, alkyl having from 1 to 4 carbon atoms, alkoxy having from 1 to 4 carbon atoms, alkanoyl having from 2 to 4 carbon atoms, alkenyl having from 2 to 4 carbon atoms, amino and nitro;

$R_3$ is a member selected from the group consisting of hydrogen, halogen, alkyl having from 1 to 4 carbon atoms, alkoxy having from 1 to 4 carbon atoms and, together with $R_2$ in the ortho-position, —CH=CH—CH=CH— or —(CH$_2$)$_n$— where $n$ is an integer from 3 to 5;

$R_4$ is a member selected from the group consisting of hydrogen and alkyl having from 1 to 3 carbon atoms; and $R_5$ is a member selected from the group consisting of alkyl having from 1 to 3 carbon atoms, and, together with $R_4$, —(CH$_2$)$_p$—, where $p$ is an integer from 4 to 6;

and physiologically compatible acid addition salts thereof.

2. A composition of claim 1, where $R_4$ and $R_5$ are methyl, and $R_1$, $R_2$ and $R_3$ have the meanings defined in claim 1.

3. A composition of claim 1, where $R_1$ is a member selected from the group consisting of alkenyl having from 2 to 5 carbon atoms, alkynyl having from 2 to 5 carbon atoms, alkenyloxy having from 3 to 6 carbon atoms, and alkynyloxy having from 3 to 6 carbon atoms; $R_2$ and $R_3$ are members selected from the group consisting of hydrogen and alkyl having from 1 to 4 carbon atoms, and $R_4$ and $R_5$ have the meanings defined in claim 1.

4. A composition of claim 3, where $R_4$ and $R_5$ are methyl.

5. A composition of claim 1, where $R_1$ is a member selected from the group consisting of allyl, ethynyl, propynyl, allyloxy and propargyloxy, $R_2$ and $R_3$ are hydrogen and $R_4$ and $R_5$ are methyl.

6. A composition of claim 5, where $R_1$ is in the 2-position of the propanolamine side chain.

7. A composition of claim 1, where $R_1$ is hydroxyalkyl having from 1 to 3 carbon atoms, $R_2$ and $R_3$ are hydrogen and $R_4$ and $R_5$ have the meanings defined in claim 1.

8. A composition of claim 7, where $R_1$ is hydroxymethyl.

9. A composition of claim 7, where $R_4$ and $R_5$ are methyl.

10. A composition of claim 1, where $R_1$ is amino, $R_2$ and $R_3$ are members selected from the group consisting of hydrogen, halogen and alkyl having from 1 to 4 carbon atoms, and $R_4$ and $R_5$ have the meanings defined in claim 1.

11. A composition of claim 1, where $R_1$ is 3-ethynyl, $R_2$ and $R_3$ are hydrogen and $R_4$ and $R_5$ are methyl.

12. A composition of claim 1, where $R_1$ is 2-allyl, $R_2$ and $R_3$ are hydrogen and $R_4$ and $R_5$ are methyl.

13. A composition of claim 1, where $R_1$ is amino, $R_2$ is 3-bromo, $R_3$ is 5-bromo, and $R_4$ and $R_5$ are methyl.

14. A composition of claim 1, where $R_1$ is 2-hydroxymethyl, $R_2$ and $R_3$ are hydrogen and $R_4$ and $R_5$ are methyl.

15. A composition of claim 1, where $R_1$ is 3-chloro, $R_2$ and $R_3$ are hydrogen and $R_4$ and $R_5$ are methyl.

16. The method of inhibiting the action of adrenergic nerves or lowering the blood pressure in a warm-blooded animal in need thereof, where comprises perorally, parenterally or rectally administering to said animal an effective adrenolytic or hypotensive amount of a 1-aryloxy-2-hydroxy-3-alkynylamino-propane selected from the group consisting of racemic or optically active compounds of the formula

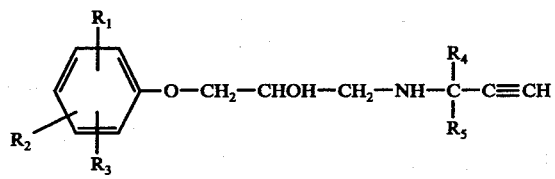

wherein $R_1$ is a member selected from the group consisting of hydrogen; halogen; nitro; alkyl having from 1 to 5 carbon atoms; alkoxy having from 1 to 4 carbon atoms; alkenyl having from 2 to 5 carbon atoms; alkynyl having from 2 to 5 carbon atoms; alkylamino having from 1 to 5 carbon atoms; dialkylamino having from 1 to 5 carbon atoms in each alkyl; alkoxyalkyl having from 2 to 6 carbon atoms; alkylaminoalkyl having from 2 to 6 carbon atoms; dialkylaminoalkyl having from 3 to 12 carbon atoms; —(CH$_2$)$_x$—NH$_2$ or —(CH$_2$)$_x$—OH, where $x$ is an integer from 0 to 3; alkynyloxy having from 3 to 6 carbon atoms; alkenyloxy having from 3 to 6 carbon atoms; —CO—R$_9$, where R$_9$ is a member selected from the group consisting of alkyl having 1 to 6 carbon atoms, phenylalkyl having 7 to 10 carbon atoms and phenyl; cycloalkyl having from 3 to 7 carbon atoms; phenyl; phenyl substituted with a substituent selected from the group consisting of halogen, lower alkyl, lower alkoxy and nitro; phenoxy; and phenoxy substituted with a substitutent selected from the group consisting of halogen, lower alkyl, lower alkoxy and nitro;

$R_2$ is a member selected from the group consisting of hydrogen, halogen, alkyl having from 1 to 4 carbon atoms, alkoxy having from 1 to 4 carbon atoms, alkanoyl having from 2 to 4 carbon atoms, alkenyl having from 2 to 4 carbon atoms, amino and nitro;

$R_3$ is a member selected from the group consisting of hydrogen, halogen, alkyl having from 1 to 4 carbon atoms, alkoxy having from 1 to 4 carbon atoms and, together with $R_2$ is the ortho-position, —CH=CH—CH=CH— or —(CH$_2$)$_n$—, where $n$ is an integer from 3 to 5;

$R_4$ is a member selected from the group consisting of hydrogen and alkyl having from 1 to 3 carbon atoms; and $R_5$ is a member selected from the group consisting of alkyl having from 1 to 3 carbon atoms, and together with $R_4$, —(CH$_2$)$_p$—, where p is an integer from 4 to 6;

and physiologically compatible acid addition salts thereof.